(12) United States Patent
Blair et al.

(10) Patent No.: US 6,834,647 B2
(45) Date of Patent: Dec. 28, 2004

(54) REMOTE CONTROL AND TACTILE FEEDBACK SYSTEM FOR MEDICAL APPARATUS

(75) Inventors: Mark S. Blair, Verona, WI (US); Robert E. Braatz, Sun Prairie, WI (US); James N. Mashak, Sun Prairie, WI (US); Norman A. Rick, Mt. Horeb, WI (US); Robert Q. Tham, Middleton, WI (US); Ronald L. Tobia, Sun Prairie, WI (US)

(73) Assignee: Datex-Ohmeda, Inc., Madison, WI (US)

( * ) Notice: Subject to any disclaimer, the term of this patent is extended or adjusted under 35 U.S.C. 154(b) by 258 days.

(21) Appl. No.: 09/924,148

(22) Filed: Aug. 7, 2001

(65) Prior Publication Data

US 2003/0029451 A1 Feb. 13, 2003

(51) Int. Cl.[7] .................................................. A62B 7/00
(52) U.S. Cl. ........................... 128/204.18; 128/200.24; 128/204.21
(58) Field of Search ........................ 128/200.14, 200.24, 128/203.12, 203.14, 204.18, 205.24, 207.14–207.18, 204.21–204.23, 204.29, 903, 904, 905, 920; 606/1

(56) References Cited

U.S. PATENT DOCUMENTS

| 3,256,876 A | 6/1966 | Elam |
| 3,874,378 A | 4/1975 | Isaacson et al. |
| 3,890,967 A | 6/1975 | Elam et al. |
| 3,973,564 A | 8/1976 | Carden |
| 4,187,845 A | 2/1980 | Dror |
| 4,991,576 A | 2/1991 | Henkin et al. |
| 5,231,981 A | 8/1993 | Schreiber et al. |
| 5,507,280 A | 4/1996 | Henkin et al. |
| 5,537,999 A | 7/1996 | Dearman et al. |
| 5,564,416 A | 10/1996 | Jones |
| 5,628,305 A | 5/1997 | Melker |
| 5,651,361 A | 7/1997 | Dearman et al. |
| 5,694,924 A | 12/1997 | Cewers |
| 5,711,295 A | 1/1998 | Harris, II |
| 5,868,133 A * | 2/1999 | DeVries et al. ......... 128/204.21 |
| 5,975,078 A | 11/1999 | Pauley |
| 6,036,662 A | 3/2000 | Van Brunt et al. |
| 6,459,933 B1 * | 10/2002 | Lurie et al. ..................... 607/5 |
| 2002/0133061 A1 * | 9/2002 | Manetta ...................... 600/300 |

FOREIGN PATENT DOCUMENTS

| WO | 99/62403 | 12/1999 |
| WO | 00/67827 | 11/2000 |

OTHER PUBLICATIONS

Photograph—44th Annual Design Review—RD 98.

* cited by examiner

Primary Examiner—Glenn K. Dawson
(74) Attorney, Agent, or Firm—Andrus, Sceales, Starke & Sawall, LLP (57) ABSTRACT

A remote control and tactile feedback system for a medical apparatus, such as a patient ventilator. The ventilator provides a signal having a property indicative of a desired parameter, such as airway pressure or tidal volume. The system has a member suitable for being received in the hand of a user, such as a clinician. A movable trigger is suitable for being engaged by the fingers of the user. An electrical-mechanical, pneumatic, or hydraulic force applying element is coupled to the trigger for applying a force to the fingers of the user responsive to the parameter signal. A tactile sensation of the desired parameter is thus provided to the user. The trigger is coupled to a signal generator for providing a control signal to the ventilator.

81 Claims, 9 Drawing Sheets

REMOTE CONTROL AND TACTILE FEEDBACK SYSTEM FOR MEDICAL APPARATUS

BACKGROUND OF THE INVENTION

The present invention relates to a system providing remote control to medical apparatus, such as a respiratory ventilator for a patient. The system also provides a tactile expression of a parameter relating to a patient or a medical apparatus to a user of the apparatus. For example, the system may provide a tactile indication of a breathing characteristic of a patient connected to a ventilator to a clinician using the system.

In one aspect of the system of the present invention, a manual member has a handle with a moveable, trigger-like member. The handle and trigger are gripped by the user. When the trigger is squeezed by the user, a signal generator is operated to provide a control signal, through a cable or other suitable means, to the ventilator for use in controlling the apparatus. For example, the control signal may be used to control the supply of breathing gases to a patient.

Medical equipment, such as a ventilator, includes sensors providing signals corresponding to various parameters relating to a patient or the apparatus. In another aspect of the invention, a signal corresponding to a parameter, for example patient airway pressure, may be returned, or fed back, from the apparatus to a manual member having a trigger. The feedback signal drives an actuator for the trigger to cause the trigger to exert a force on the fingers of the user that indicates to the user the breathing characteristic of the patient.

In a preferred embodiment of the system, a single manual member is used for both control and feedback purposes.

Respiratory ventilators provide breathing gases to a patient via a breathing circuit. The breathing circuit typically has an inspiratory limb and an expiratory limb. One end of each of the inspiratory and expiratory limbs are connected to the ventilator. The other ends are connected to a Y-connector and through a patient limb to the patient. Pneumatic elements in the ventilator periodically provide breathing gases to the patient through the inspiratory limb during inhalations. On expirations, the breathing gases are discharged from the lungs of the patient into the expiration limb. Controls in the ventilator establish parameters, such as breaths/minute, tidal volume, maximum pressures, etc. that characterize the ventilation provided to the patient by the ventilator.

A patient may also be manually ventilated by means of a flexible container or "bag" provided on the ventilator. The bag is filled with breathing gases and manually squeezed by a clinician to provide breathing gases to the patient. Use of the bag, or "bagging the patient," is often required or preferred by clinicians as it enables the clinician to physically control the delivery of breathing gases to the patient. Equally important, the feel of the bag as it is manipulated by the clinician enables the clinician to sense conditions in the lungs and respiration of the patient. In the hands of a skilled clinician, subtle characteristics and/or changes in the lungs and respiration can be sensed. It is difficult or impossible to obtain this type of feedback information when mechanical ventilating apparatus provides the breathing gases.

For the foregoing reasons, patients are often bagged during surgical procedures when anesthesia is induced in the patient by entraining an anesthetic in the breathing gases. Another environment in which patients are often bagged is in an intensive care unit.

However, if bagging is carried out for a long time, it becomes fatiguing to the clinician lessening both the fineness of the control of breathing gas supply and the sensing of lung or other respiratory conditions affecting the subject.

Also, the bag is usually positioned at a fixed location on the ventilator. This restricts the degree to which the clinician, when bagging a patient, can move about the patient, for example, to observe a surgical patient positioned in a manner appropriate to the surgery to be performed. The same is true when the pneumatic elements of the ventilator, rather than the bag, are providing the breathing gases to the patient since the controls necessary to operate the pneumatic elements are placed at a fixed location on the ventilator.

SUMMARY OF THE PRESENT INVENTION

It is, therefore, an object of the present invention to provide a system that enables a clinician, or other user to remotely control medical apparatus, such as a ventilator. The invention may also remotely provide a tactile sensory indication of a parameter, such as a respiratory parameter of a patient connected to a medical apparatus.

The fact that the system is remote, allows the clinician, or other user for the system to move with respect to the apparatus to which the system is connected and with respect to a patient being treated by the apparatus, thereby to improve the effectiveness of care provided to the patient.

In applications involving a respiratory parameter, the system of the present invention provides a control operation and feedback sensation resembling that experienced by a clinician when manually feeling the bag. This enables the clinician to sense and control conditions in the patient in a highly effective manner. However, the system of the present invention avoids the fatigue incurred with manually bagging the patient. The sensing and control provided by the present invention can be enhanced by adjusting the sensitivity and linearity between the control and feedback signals and the resulting control action and tactile sensation generation. This enables an optimal relationship to be established between user input and ventilation delivery for a particular patient.

While the foregoing has described the present invention in connection with sensing ventilation parameters, it may also be used to provide a tactile feedback of other parameters. For example, the system may be used to provide a tactile indication of the cardiac properties, such as blood pressure or pulse rate.

Briefly, the present invention provides a remote feedback system for providing a tactile expression of a characteristic of a parameter of an apparatus to which the system is connected. The apparatus provides a feedback signal indicative of the parameter. The system typically includes a member having a moveable trigger. An electro-mechanical, or fluidic force applying actuator, such as a linear motor, is coupled to the trigger. The feedback signal is provided to the actuator by a communication means, such as a cable or telemetry link. When the member and trigger are gripped by the user, the forces exerted on the fingers of the user by the trigger, as the trigger is driven by the actuator, are an indication of a characteristic of the parameter of the apparatus.

By providing the system with a potentiometer, or other signal generator, operated by the trigger, the system can also provide a signal to control the operation of ventilator apparatus via the communication means.

Various other features, objects, and advantages of the invention will be made apparent from the following detailed description and the drawings.

BRIEF DESCRIPTION OF THE DRAWING

The invention will be further understood from the following detailed description taken in conjunction with the drawing.

In the drawing.

DETAILED DESCRIPTION OF THE PREFERRED EMBODIMENT

Figure 1:
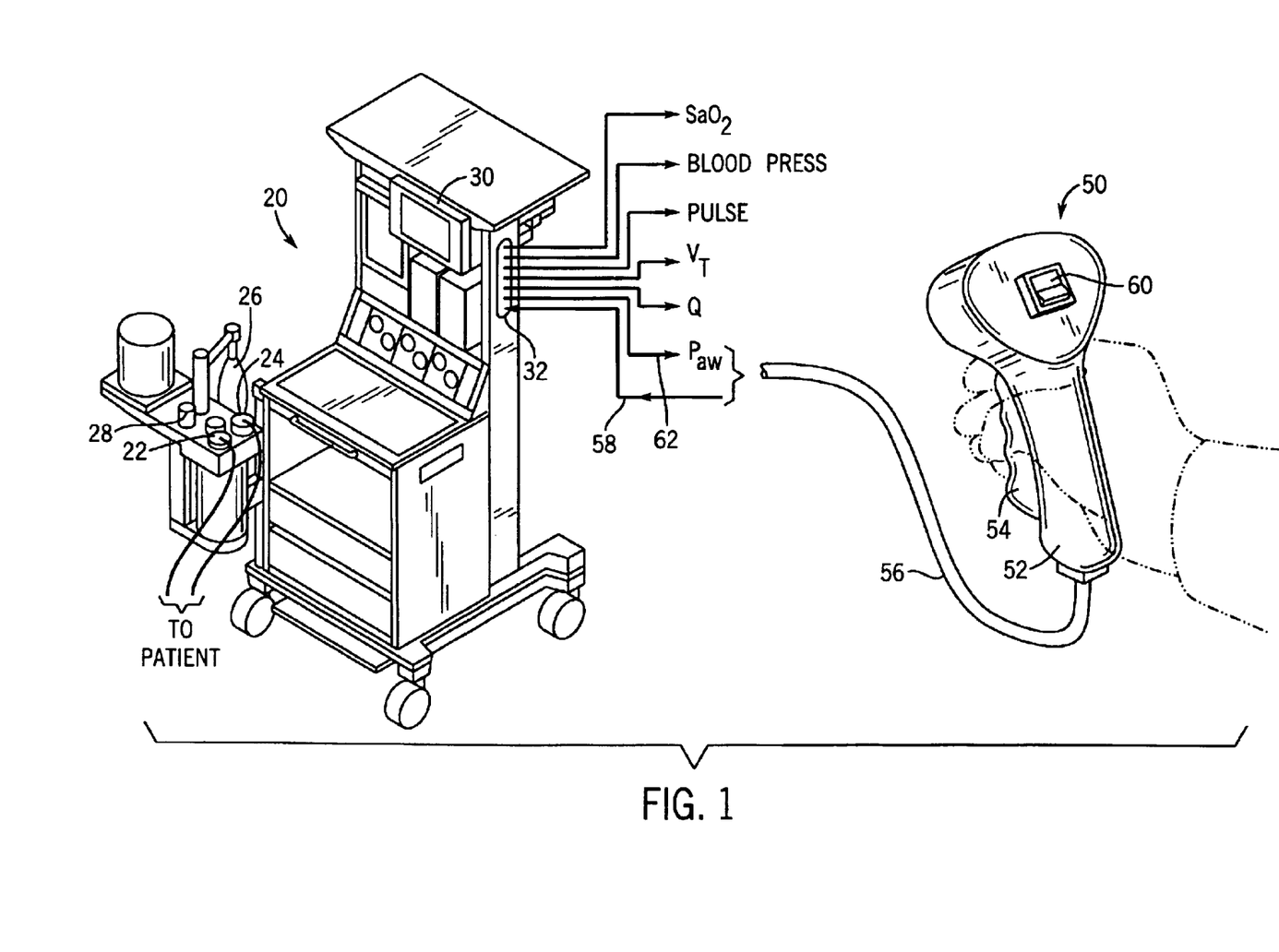
FIG. 1 shows a basic embodiment of the remote control and tactile feedback system of the present invention in use with medical apparatus comprising a ventilator.

Medical apparatus suitable for use with the system of the present invention is shown in FIG. 1 as ventilator 20 incorporated in an anesthesia machine. Ventilator 20 has connectors 22 and 24 suitable for connection to the inspiratory and expiratory limbs of a breathing circuit leading to a patient, as diagrammatically shown in FIG. 1. Ventilator 20 provides breathing gases to the patient in the inspiratory limb of the breathing circuit and receives gases expired by the patient in the expiratory limb.

Ventilator 20 is provided with bag 26 for manually bagging the patient. Switch 28 is operated to allow bag 26 to provide breathing gases to the patient.

Ventilator 20 receives inputs from sensors associated with the patient and/or ventilator 20. The data contained in these inputs may be displayed on patient monitor 30. Data relating to the sensed parameters is also provided to terminal 32. Typical data outputs are shown as patient airway pressure $P_{aw}$, tidal volume $V_T$, breathing gas flow rate Q, pulse rate, blood pressure, and arterial blood oxygen saturation $SaO_2$ parameters.

FIG. 1 also shows member 50 of the remote control and tactile feedback system of the present invention. As shown generally in FIG. 1, member 50 includes grip or handle 52 suitable for received in the hand of a clinician or other user. Trigger 54 is mounted in handle 52 so that the fingers of the user may extend around the exposed edge of the trigger. Trigger 54 pivots with respect to handle 52. Member 50 may be coupled to an apparatus, such as ventilator 20, by cable 56.

Member 50 may be provided with a switch 60 connected, via conductors in cable 56, to apparatus 20 to remotely control apparatus 20 as indicated diagrammatically at 58 in FIG. 1. Actuation of switch 60 may carry out a desired operation of the ventilator. For example, repetitive actuation of switch 60 will cause the ventilator to provide a given quantity of breathing gases to the patient each time the switch is actuated.

In a preferred embodiment of the invention, described in detail, below, a signal generator is connected to trigger 54 and movement of the trigger by the fingers of the operator provides a control signal to remotely control the ventilator. The signal generator may, for example, comprise a switch, a potentiometer or a rheostat. Switch 60 may then comprise an on-off switch to cause ventilator 20 to be operated in the ordinary manner or under the control of member 50.

Cable 56 also contains a conductor providing, or feeding back, a signal corresponding to one of the parameters outputted by apparatus 20. In the example shown in FIG. 1, patient airway pressure $P_{aw}$ is fed back, as diagrammatically indicated at 62. The signal corresponding to parameter 62 is provided to a tactile feedback generator or actuator in member 50 for trigger 54 that applies corresponding force to the fingers of the user holding member 50. This provides a tactile indication or impression to the operator of the parameter that is fed back from the medical apparatus.

With member 50 coupled to apparatus 20 via cable 56, it will be appreciated, that the clinician or other user can move about the apparatus and patient to a desired location, while at the same time maintaining control over the operation of ventilator 20 and receiving the tactile feedback corresponding to a desired parameter.

Figure 2:
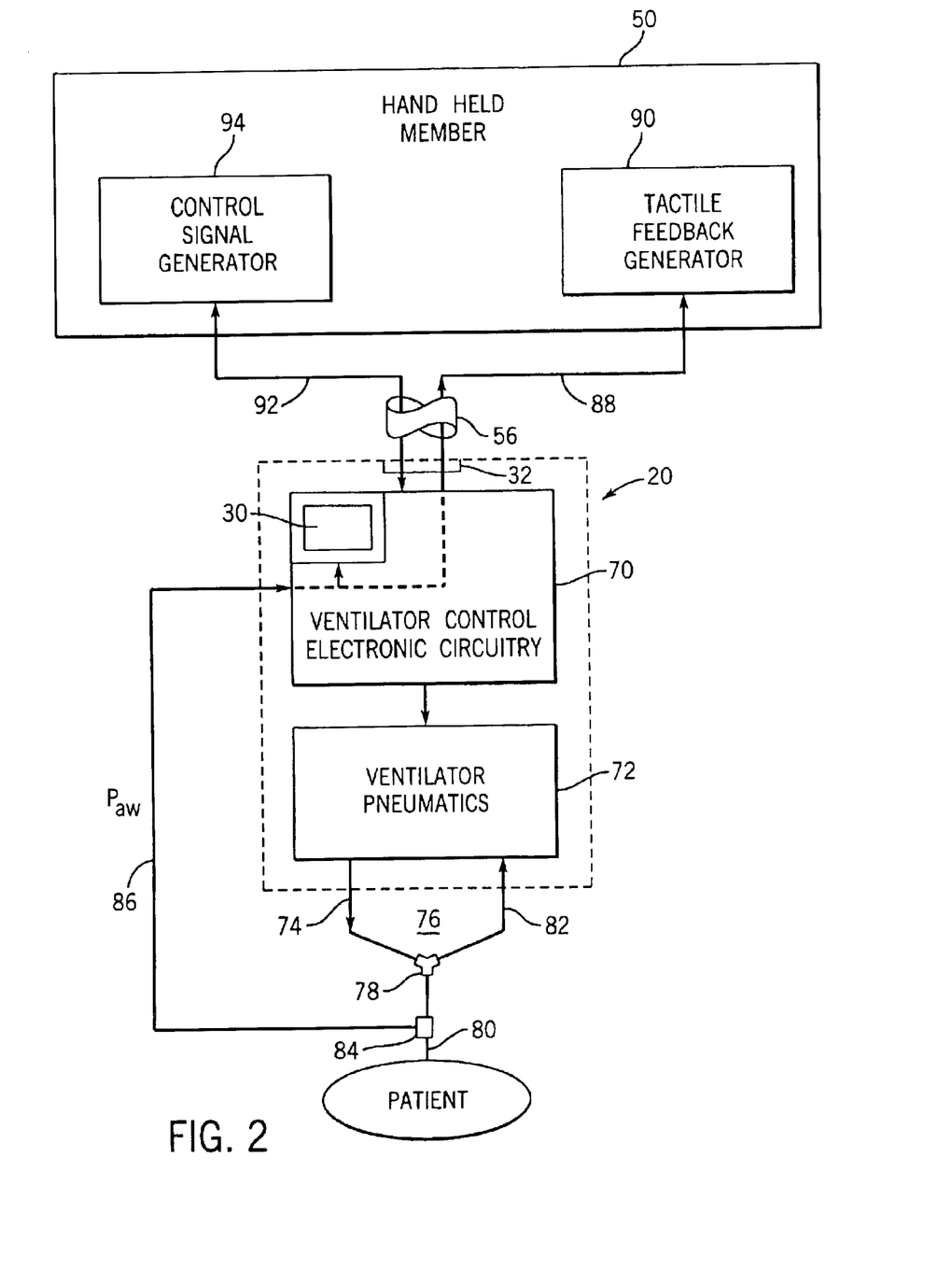
FIG. 2 is a schematic diagram of the system of the present invention in conjunction with ventilator apparatus.

FIG. 2 shows a schematic diagram of member 50 in conjunction with an apparatus 20 comprising a ventilator for a patient. Ventilator 20 includes electronic control circuitry 70 that operates ventilator pneumatic circuitry 72. Pneumatic circuitry 72 comprises a source of pressurized gas that provides breathing gases in inspiratory limb 74 of a patient breathing circuit 76. Pneumatic circuitry 72 may provide breathing gases directly to the lungs of the patient, as in a typical critical care application. Or, a driving gas provided by pneumatic circuitry 72 may compress a bellows containing the breathing gases which, in turn, supplies the gases to the patient, as in a typical anesthesia application. The breathing gases pass through Y-connector 78 to patient limb 80 for supply to the patient. The breathing gases are returned to ventilator 20 in expiratory limb 82. In the embodiment shown in FIG. 2, pressure sensor 84 provides an airway pressure $P_{aw}$ signal in conductor 86 to ventilator control electronic circuitry 70. The signal in conductor 86 is proportional to the pressure in patient limb 80 leading to the lungs of the patient. Ventilator control electronic circuitry 70 may include monitor 30 that provides a numeric or graphic display of patient airway pressure $P_{aw}$, as well as other patient or apparatus parameters. The signal from airway pressure sensor 84 is also provided in conductor 88 of cable 56 to member 50. The signal in conductor 88 is supplied to tactile feedback generator 90 to operate trigger 54 in a manner to provide a tactile expression of the magnitude of the patient airway pressure $P_{aw}$ to the fingers of the user engaging trigger 54.

Cable 56 also includes conductor 92 connected to control signal generator 94 for use in controlling ventilator 20. As noted above, control signal generator may comprise switch 60 or a signal generator, such as a potentiometer, operable by trigger 54.

Figure 3:
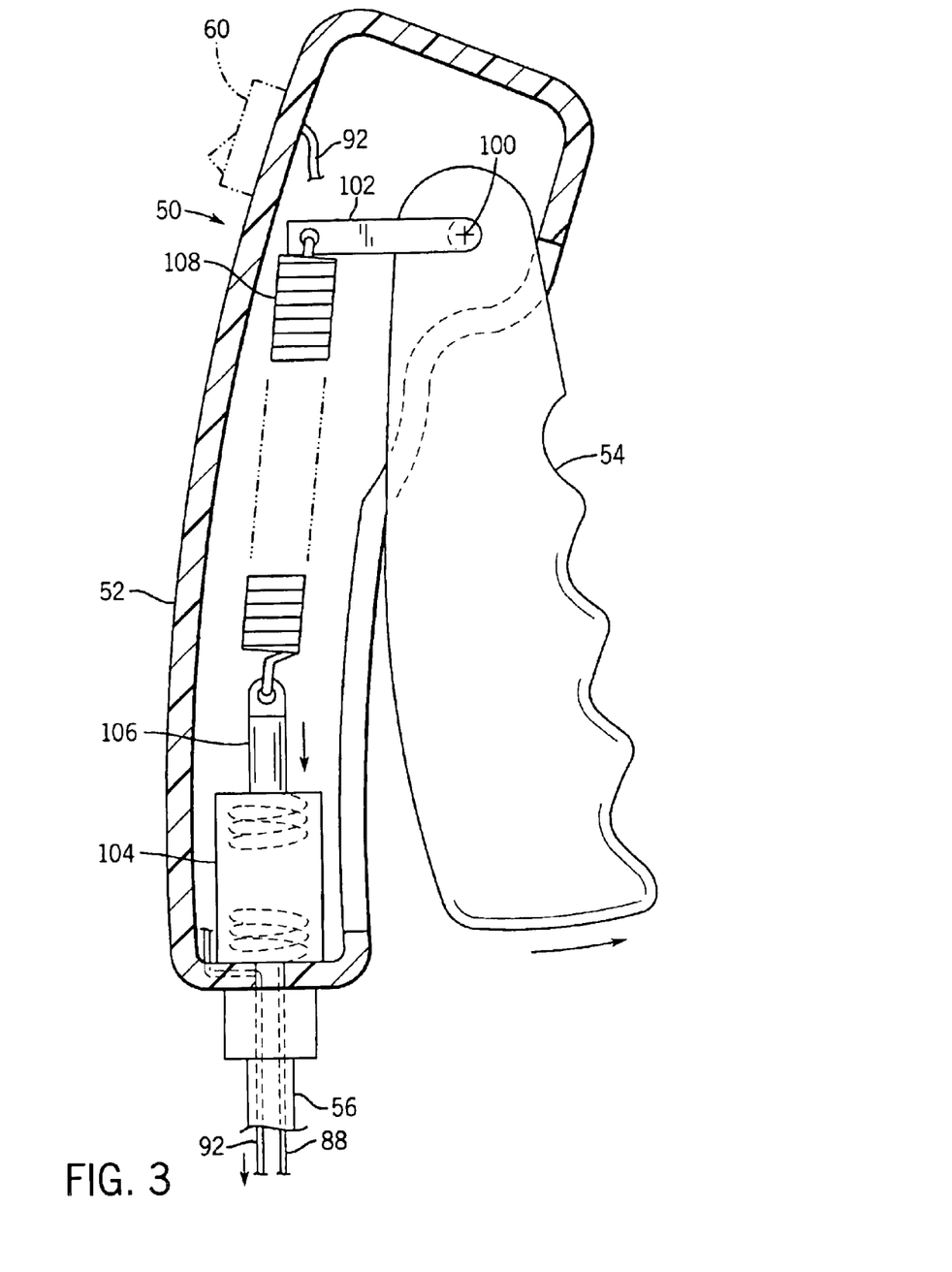
FIG. 3 shows one embodiment of a manual member of the system having elements providing a mechanically generated tactile feedback sensation to a user.

FIG. 3 shows one construction for member 50. Member 50 includes switch 60 connected to conductor 92 for controlling ventilator 20 or for turning the system on or off. Trigger 54 is affixed to shaft 100 that is journaled in handle 52. Arm 102 extends from shaft 100. Electromagnetic actuator 104 comprises armature 106 extending from a coil of wire in the actuator. The coil surrounds armature 106 and is connected to conductor 88. The exposed end of armature 106 is connected via spring 108 to arm 102 to form the tactile feedback generator 90 shown in FIG. 2

When actuator 104 is energized by the feedback signal from apparatus 20 in conductor 88, armature 106 is drawn into the coil of wire in the actuator 104 in the well known manner of a solenoid, as shown by the arrow in FIG. 3. This movement exerts a force on the end of arm 102 tending to cause trigger 54 to rotate in the clockwise direction also as shown in FIG. 3. When member 50 is held in the hand of a user, with handle 22 in the palm of the user's hand and the fingers of the operator extending around the trigger 24, as shown in FIG. 1, the force urging the clockwise rotation of trigger 54 will be felt as a tactile sensation on the inner surfaces of the fingers of the user. The magnitude of the sensation will be proportional to the degree of actuation of the coil of actuator 104 and hence the magnitude of the signal in conductor 88 and the sensed parameter. The experience to the clinician or other user will thus resemble that of manipulating a ventilator bag so that the user has a "feel" of the ventilation being provided to a patient.

As noted above, switch 60 in member 50 may be used to render member 50 operative or as inoperative. Or, switch 60 may be used to operate apparatus 20, for example, to deliver a preset volume of breathing gas to the patient connected to the ventilator over a given period of time. Or, switch 60 can be used to select the parameter that is to be indicated in a tactile manner. For example, the switch may be used to operate circuitry located in member 50 or apparatus 20 to select tidal volume $V_T$ as the monitored parameter for which a tactile expression is provided. Switch 60 may be of any type suitable for the desired purpose, such as a thumbwheel switch, a sliding switch, or a rotary switch.

Figures 3A, 3B:
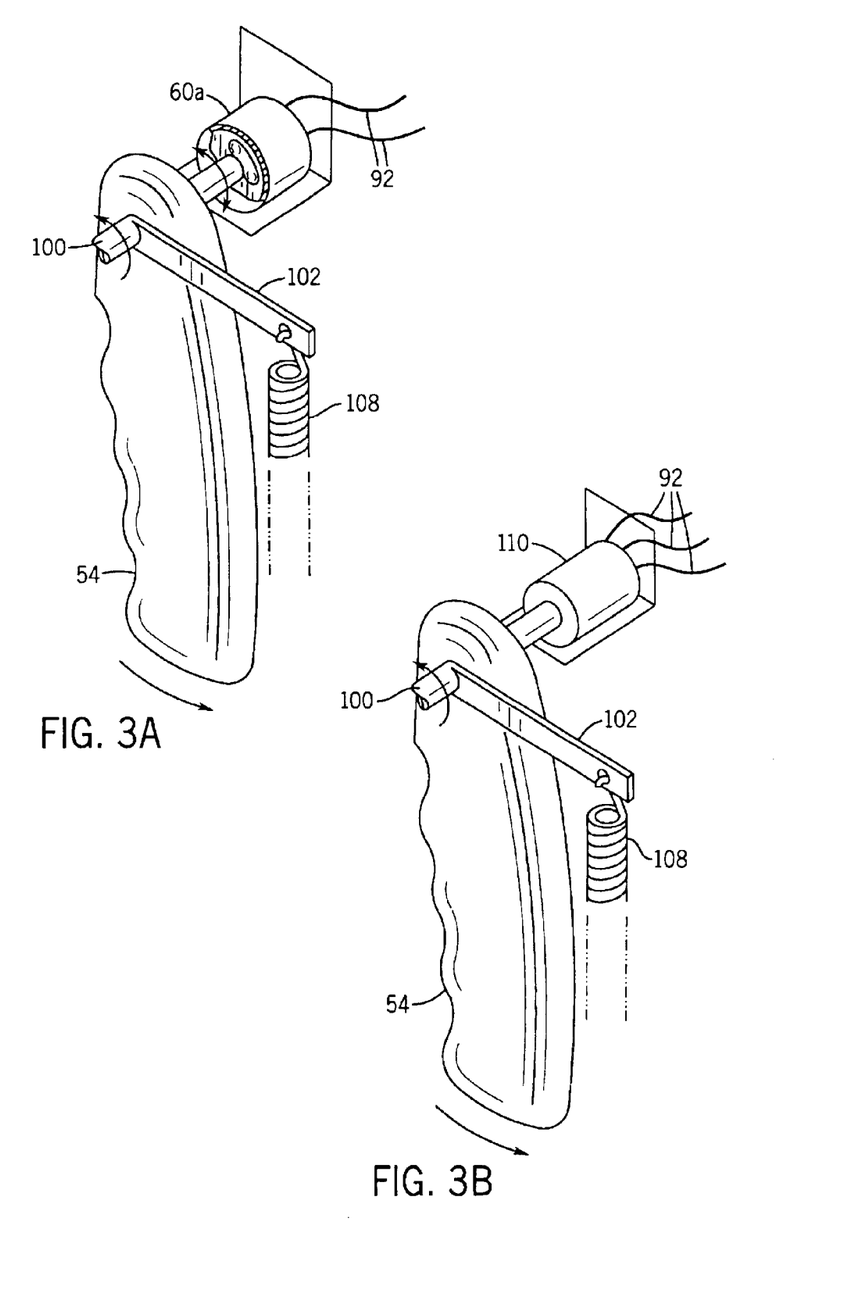
FIG. 3A shows a modification of the manual member having elements for remotely controlling the apparatus to which the manual member is connected.
FIG. 3B shows a further embodiment of a manual member.

In another embodiment of member 50, the control element may be mounted in member 50 in a manner such that it can operated when the trigger 54 is moved into member 52 when the user squeezes trigger 54. For this purpose, a rotary switch, such as switch 60a, may be mounted on shaft 100, as shown in FIG. 3A. When trigger 54 is squeezed by the hand of the user, the trigger is moved in the counter clockwise direction shown in FIG. 3A, to operate the switch.

FIG. 3B shows a further modification of member 20 in which the wiper of potentiometer 110 is coupled to shaft 100. Potentiometer 110 provides a variable magnitude signal in conductors 92 that is proportional to the movement of trigger 54. This enables member 50 to provide a variable control action in apparatus 20.

In the operation of member 50 shown in FIG. 3B, member 50 is placed, as described above, in the hand of the user with the handle 52 resting in the palm and the fingers extending around trigger 54. The user squeezes trigger 54. This rotates trigger 54 in the counter clockwise direction, when the trigger is viewed as in FIG. 3B. It also rotates shaft 100, and the wiper of potentiometer 110 to provide a signal in conductors 92 to the ventilator control circuitry 70 via cable 56. The magnitude of the signal provided to circuitry 70 is proportional to the rotary movement or displacement of trigger 54. Control circuitry 70 operates ventilator pneumatic circuitry 72 to provide a flow of breathing gases from ventilator 20 into inspiratory limb 74 to the patient.

Pressure sensor 84 provides a signal in conductor 86 corresponding to the airway pressure $P_{aw}$ in patient limb 80 resulting from the breathing gas flow. This signal is provided via cable 56 and conductor 88 to tactile feedback generator 90, such as electromagnetic actuator 104, in member 50. In the manner described above, this operates actuator 104 to urge trigger 54 in the clockwise direction of rotation when viewed as in FIG. 1. A force will be felt by the fingers of the user engaged with the trigger 54. The greater the patient airway pressure $P_{aw}$, the greater will be the force felt by the user. The magnitude of the tactile sensation incurred by the user thus provides a feedback indication of the magnitude of the patient airway pressure $P_{aw}$ in the manner of a ventilator bag.

To terminate the inspiratory phase of the respiratory cycle, the user releases trigger 54, allowing it to rotate in the counterclockwise direction when viewed as in FIG. 1. This reduces the magnitude of the signal in conductors 92 to ventilator control electronic circuitry 70 and causes ventilator pneumatic circuitry 72 to cease or reduce supplying breathing gases to the patient. This allows the expiratory phase of the respiratory cycle to commence. During the expiratory phase, airway pressures of the patient will fall. This will reduce the magnitude of the signal in conductor 88 to tactile feedback generator 90. This will correspondingly reduce the force applied to trigger 54 by actuator 104 so that the user has a tactile sense that the airway pressure of the patient has decreased. If desired, trigger 54 may be only partially released so as to provide a positive end expiratory pressure (PEEP) or other desired ventilation protocol in the lungs of the patient.

It will be appreciated from the foregoing explanation, that member 50 shown in FIG. 3B thus operates in a manner analogous to the conventional bag provided on a ventilator. That is, by squeezing trigger 54, a clinician can deliver breathing gases to the patient. This resembles manually squeezing the ventilator bag. Tactile feedback generator 90 provides a resistance or a countering force on trigger 54 that corresponds to the resistance and characteristics of the breathing bag felt by the clinician when manipulating the bag.

In a preferred embodiment of the invention, the system of the present invention may be arranged, by appropriate elements in member 50 or apparatus 20 to establish the flow rate of the breathing gases to the patient proportional to the amount of rotation or angular displacement of trigger 54. This may be accomplished by linear amplification components in control generator 94, ventilator control electronic circuitry 70 and/or ventilator pneumatics 72. This approach provides an easy way for the clinician to establish both the flow rate and the volume of breathing gases delivered to the patient. The delivered volume is the amount of displacement, i.e., flow rate, multiplied by the time during which the flow rate occurs. As the patient airway pressure and tactile feedback increases during inspiration, the clinician will have to increasingly apply more force to trigger 54 in order to maintain a given breathing gas flow.

Alternately, the breathing gas flow rate may be made proportional to the rate of change of displacement of trigger 54. In this approach, the faster trigger 54 is moved, the greater the breathing gas flow rate to the patient. In order to maintain a breathing gas flow to the patient, the trigger must continue to be moved. This embodiment is directly analogous to the conventional ventilator bag. That is, in order to get a continuous flow of breathing gases from the bag to the patient, the clinician must continually squeeze the bag. If the clinician stops squeezing the bag, the flow of breathing gases stops. And further in the manner of a bag, as the patient airway and tactile feedback increases as a result of breathing gas flow to the lungs of the patient, the clinician will have to squeeze trigger 54 harder in order to maintain a given flow of breathing gases to the patient. The action also resembles that of a bag.

To obtain this mode of operation, a differentiator, or time-derivative, component may be used in connection with the signal in conductor 92. An operational amplifier having a capacitor in the input for conductor 92 may be employed.

While the system of the present invention has been described as using control signal generator 90 to control the flow or volume of breathing gases delivered to the patient, it will be appreciated that it may be used to control the pressure of the breathing gases if this mode of ventilation is desired.

By appropriate circuitry/software in member 50 or in ventilator control circuitry 70, the sensitivity of the control action provided by control signal generator 94, such a potentiometer 110, and the feedback action provided by tactile feedback generator 90 can be adjusted. Adjustable gain amplifiers may be used for this purpose. This facilitates the ventilation of patients having differing physiologies or anatomies, for example, a patient with stiff, non-compliant lungs, or a pediatric patient having very small lung volume. The sensitivity of the control action carried out responsive to the signal in conductors 92 from control signal generator 94 can be different from the sensitivity of the tactile feedback provided by tactile feedback generator 90 to trigger 54. For example, when the patient is an infant it may be desirable to have a low sensitivity for control signal generator 94 so that a large input signal to control circuitry 70 provides a relatively small amount of ventilation commensurate with the small lungs of the infant. At the same time, a high sensitivity is provided in tactile feedback generator 90 so that relatively low airway pressure produces a relatively large tactile feedback response. For an adult patient, control signal 90 may have a high sensitivity to reduce the effort required by the user to move the relatively large amount of breathing gases needed for adult patients. The ability to adjust the sensitivity of the tactile feedback generator and the control signal generator enables an optimal user input to ventilation delivery relationship for a particular patient to be established.

Also, by appropriate circuitry/software, the sensitivity of either or both of control and feedback action can be made linear or non-linear, or a combination of the two, over the operating range of the system. Thus, it may be desirable to have the tactile feedback sensation provided to the user increase as a function of patient airway pressure to provide greater sensitivity at higher pressures.

While FIG. 3 shows the use of a linear actuator for actuator 104, it will be appreciated that a rotary actuator, such as an electric motor having a torque arm on the output shaft could also be used to provide the desired tactile sensory indication.

Figure 4:
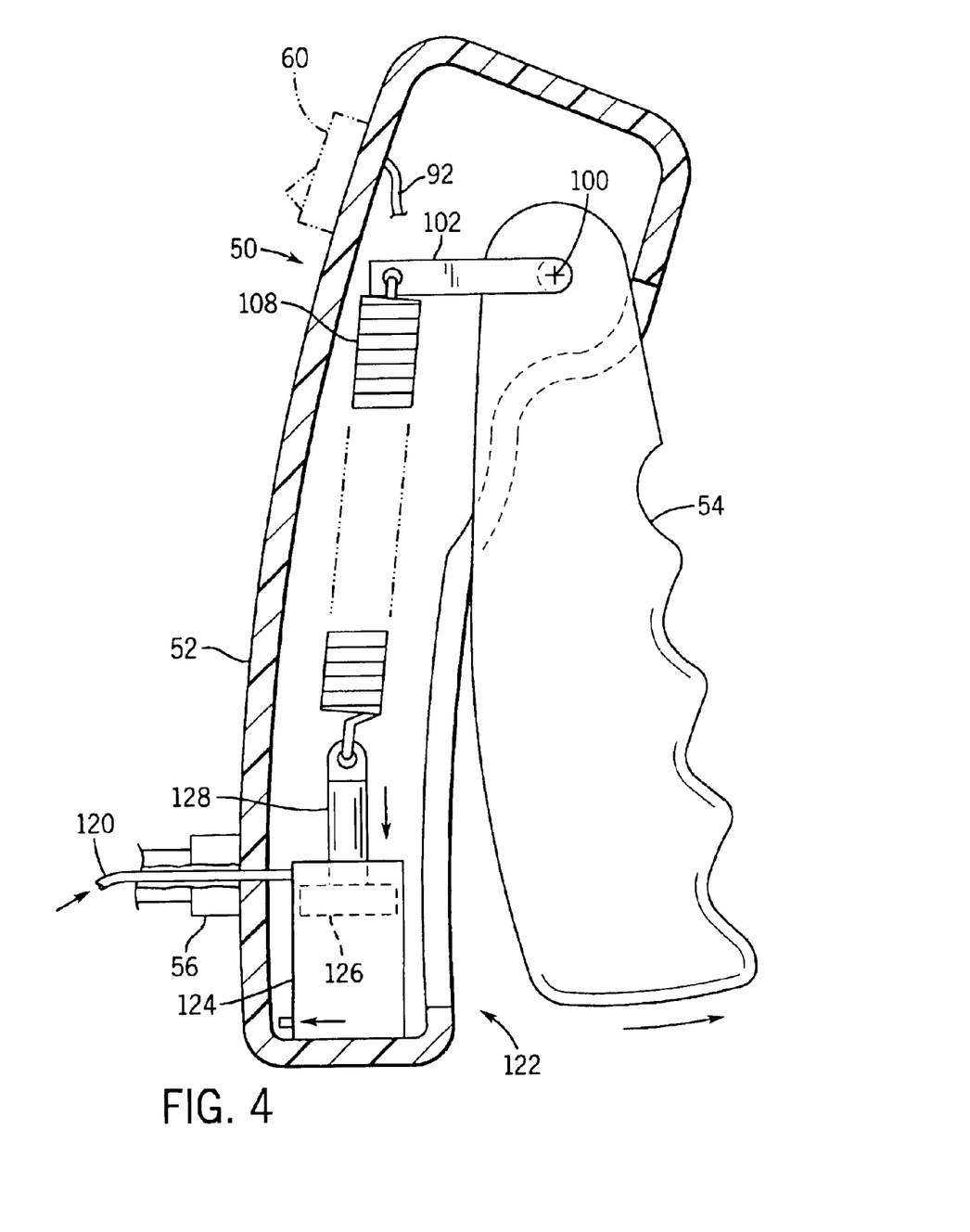
FIG. 4 shows a manual member having a fluid operated means for generating a tactile indication of a parameter.

Also, while FIGS. 3, 3A, and 3B show use of an electromagnetic actuator 104, 106 as tactile feedback generator 90 it will be appreciated that other devices can be used, if desired. FIG. 4 shows the use of an actuator employing a fluid, such as a gas or liquid. For this purpose, cable 56 includes a tube 120 for conveying the fluid to a fluid operated actuator 122 such as an cylinder 124 having piston 126 connected to piston rod 128. Piston rod 126 is connected to spring 108 in the same manner as actuator 106 shown in FIG. 3. Tube 120 receives a pressurized fluid, such as a gas, from ventilator 20 to operate actuator 122. The pressure of the fluid as supplied is proportional to the magnitude of the monitored parameter. Or, an expandable bladder that abuts trigger 54 may be used as a tactile feedback generator. Control signal generator 94 may also be a fluidic device, if desired.

FIGS. 1–3 shows the use of cable 56 to provide and receive signals to and from apparatus 20. The electrical signals may be analog, as generally described above. Or, the signals may be digital in which case tactile feedback generator 90 may be a digital stepper motor and control signal generator 94 may be a digital rotary transducer.

The necessary signals to and from member 20 may also be provided optically, in which case cable 56 will include one or more optical fibers. Photo-electric devices in member 50 and ventilator control circuit 70 provide the conversion between electrical and optical signals. Or, an optical link may use invisible light, such as infrared, to provide the necessary communication in which case cable 56 may be eliminated. Infrared sensors and receivers may be utilized in such an embodiment.

Still further, member 50 maybe coupled to apparatus 20 by a radio communications link, such as a telemetry link.

Figure 5:
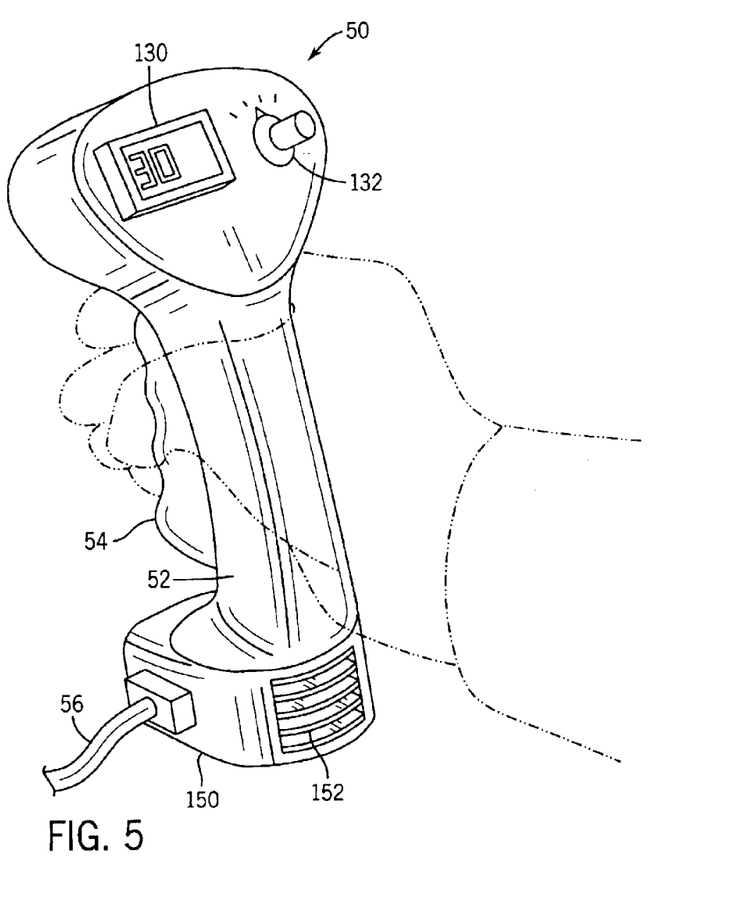
FIG. 5 shows a modification of the manual member of the system of the present invention to include a display and a base.

FIG. 5 shows an embodiment of the invention in which member 50 has display 130. Display 130 may provide a visually perceptible indication of a fedback parameter or of a control action being carried out by apparatus 20. For example, display 130 may show the magnitude of the patient airway pressure $P_{aw}$ fed back to member 50 in conductor 88. Or, display 130 may be coupled to monitor 30 in apparatus 20 to provide graphic or alpha-numeric indication of other information. Rotary switch 132 can be used to select the information to be shown in display 130 and/or to carry out certain settings in apparatus 20.

While the system of the present invention has been described above in connection with a respiratory parameter, such as patient airway pressure $P_{aw}$, other physiological parameters may be indicated in a tactile manner by the system of the present invention. For example, a signal corresponding to the heart rate or pulse of the patient may be provided in conductor 88 to tactile feedback generator 90. Such a signal comprises a series of electrical pulses. The signal will cause tactile feedback generator 90 to provide corresponding force pulsations on trigger 54 and tactile indications to the user of the system of the present invention. The sensation would be somewhat the same as feeling the pulse of a patient at his/her wrist.

It is also possible to provide tactile indications of a plurality of parameters. For example, a tactile feedback of heart rate comprised of a series of pulsations spaced in time can be superimposed on a tactile feedback of patient airway pressure.

Member 50 may be provided with a base 150, as shown in FIG. 5. The base enables member 50 to stand when placed on a flat surface. The base preferably extends beyond trigger 54 to avoid inadvertent operation of member 50 and apparatus 20, should member 50 topple over. The connection for cable 56 maybe provided in base 150. The base 150 may also contain a battery pack if necessary or desirable for the operation of the remote tactile feedback system. Base 90 may also include a heat sink 152 having fins, as shown in FIG. 5 to reduce any heat build up from actuator 104 or similar components in member 50.

In the alternative, a holster maybe provided on the medical apparatus, such as the ventilator, in which member 50 is placed when not in use.

While the remote tactile feedback system of the present invention has been shown in an embodiment in which member 50 is placed in the hand of a user, the system is not so limited. For example, member 50 could be designed to be placed on the wrist of a user as shown in FIG. 6 at 160 with a force supplying means 162, such as actuator 104-armature 106, applying pressure to the wrist of the user.

Figure 7:
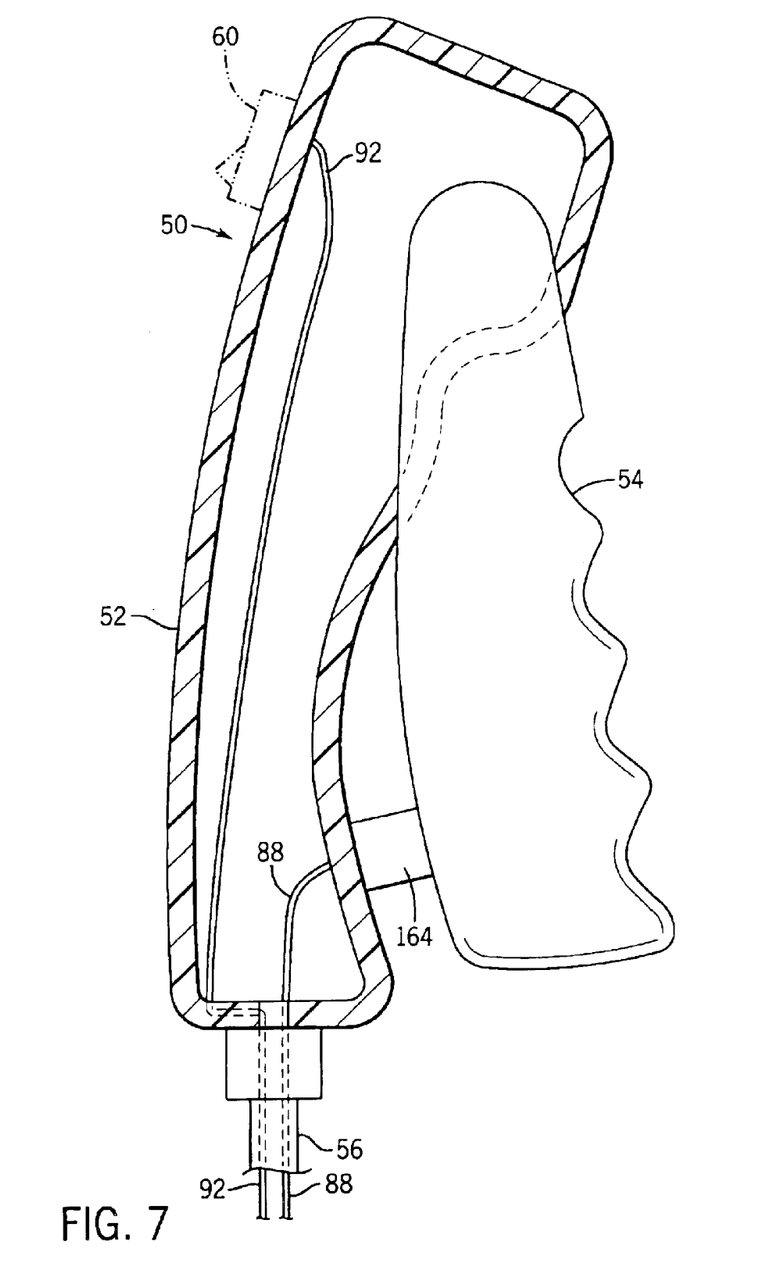
FIG. 7 shows a further modification of the manual element to include a pressure operated element.
Figure 9:
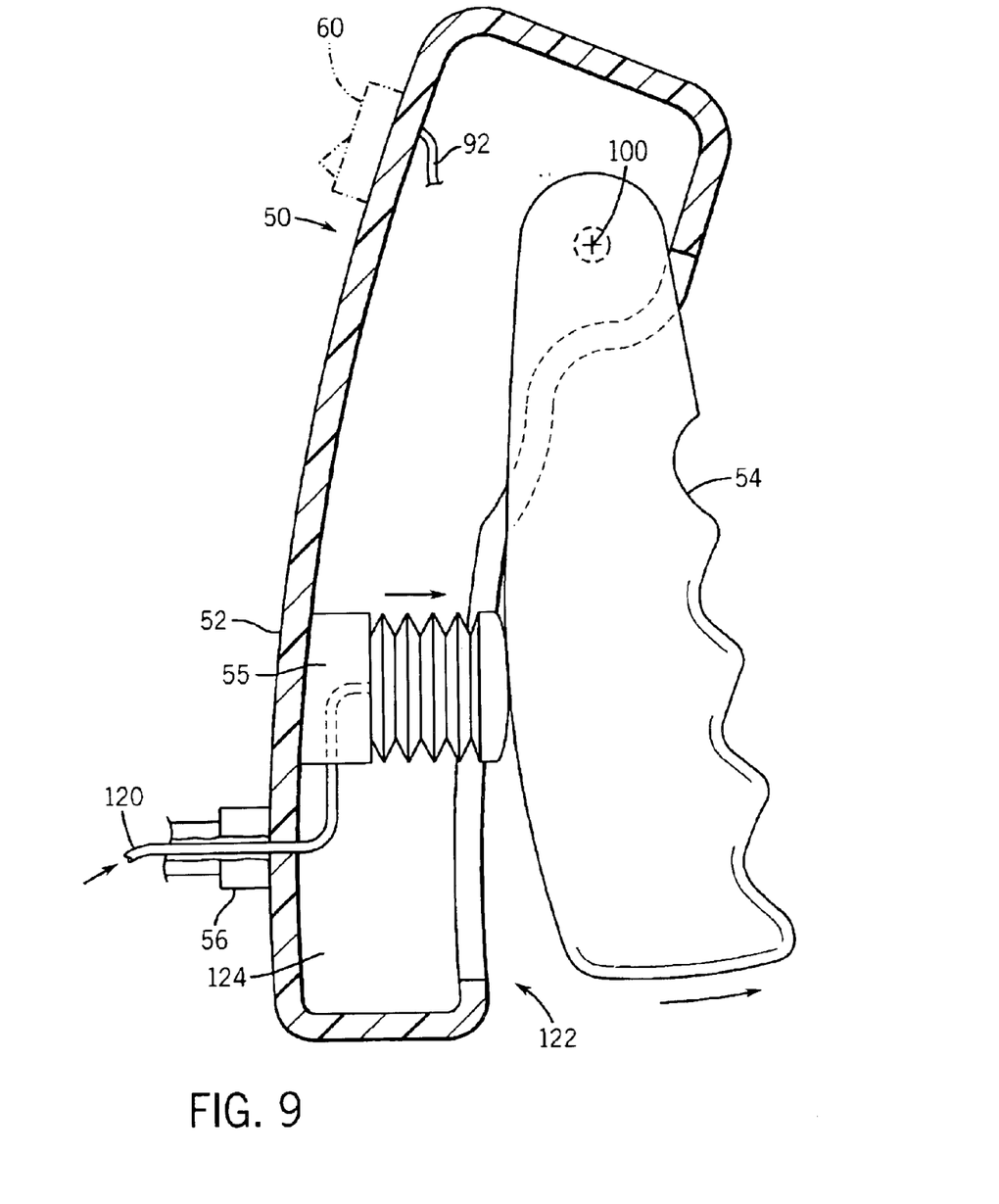
FIG. 9 shows a manual member having a fluid operated means for generating a tactile indication of a parameter.

Member 50 of the present invention has been shown in an embodiment in which the tactile feedback aspects and the control aspects are provided in a single device, such as member 50. However, it will be appreciated that tactile feedback generator and the control member maybe physically separate from each other. For example, member 50 providing the tactile feedback may be held in the hand of an operator while the control signal generator may comprise a foot, voice, or eye operated device. For example, the control signal generator may comprise a foot actuated switch or potentiometer. Further, while the system has been described above showing control signal generator 94 as having a displaceable element 164, such as trigger 54, the control signal generator may comprise a pressure operated element, such as a piezoelectric element 164 shown in FIG. 7, that senses force applied by the hand, fingers, or foot of the user.

Figures 6, 8:
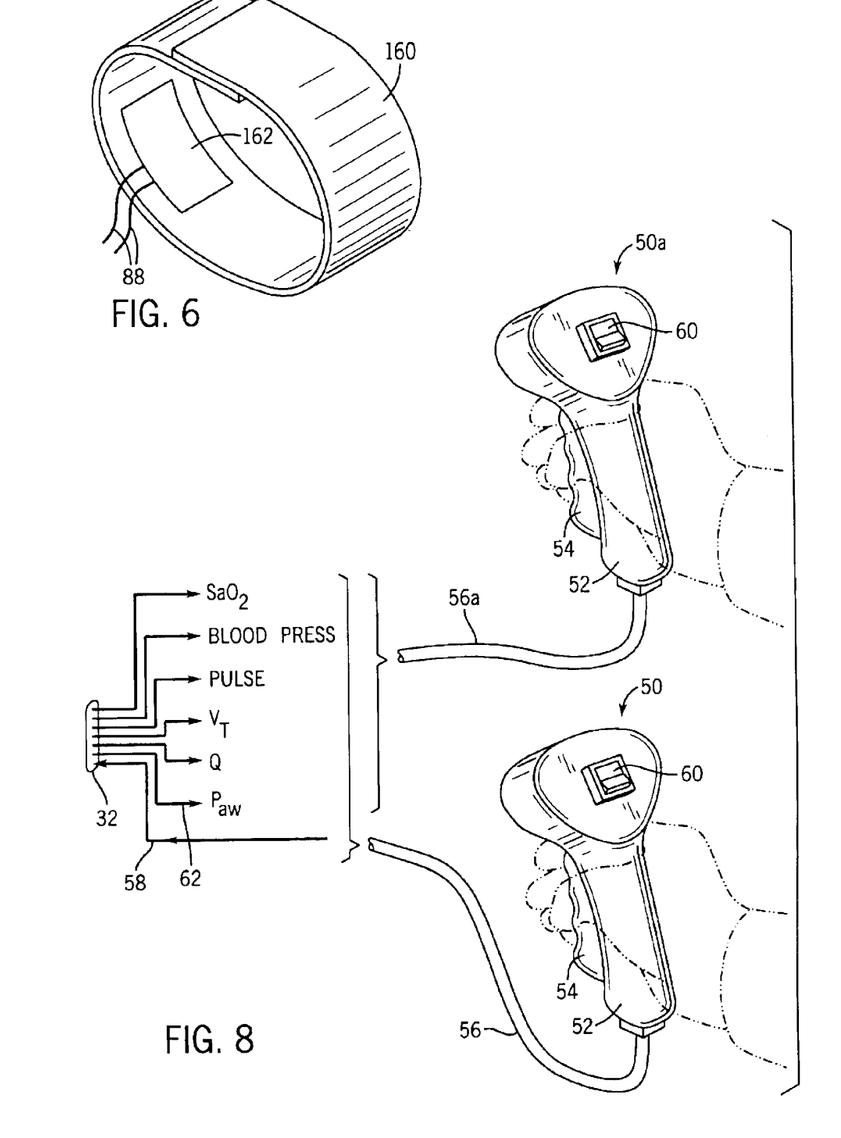
FIG. 6 shows another embodiment of elements for providing a tactile feedback sensation.
FIG. 8 shows an embodiment of the system having a plurality of manual members.

FIG. 8 shows the system of the present invention with an additional manual member 50a. Member 50a is generally in parallel with member 50 as by a connection to apparatus 20 in cable 56a, as shown in FIG. 8, or to member 50 itself. Such an arrangement may be used in a teaching setting. For example, an instructor may manipulate member 50 and a student holding member 50a will be able to also experience the tactile feedback resulting from the operation of the medical apparatus. Or, the student may operate member 50 and the instructor can monitor his or her actions with member 50a.

It is recognized that other equivalents, alternatives, and modifications aside from those expressly stated, are possible and within the scope of the appended claims.

What is claimed is:

1. A remote controller for a respiratory ventilator providing breathing gases to a patient, said controller allowing an operator to move about the ventilator and patient while controlling the ventilator, said controller comprising:

a control member actuatable by an operator to provide a signal for carrying out a control action in the ventilator;

communication means placing the control member in communication with the ventilator in a manner that allows the operator to move with respect to the ventilator and patient and to be at a distance from the ventilator, said communication means communicating said signal to the ventilator to control the ventilator; and means for adjusting the sensitivity between the signal provided by said control member and the resulting control action in the ventilator.

2. A remote controller of claim 1 wherein said control member provides a signal having a magnitude range and wherein said adjusting means alters the sensitivity over the magnitude range of the signal.

3. A remote controller for a respiratory ventilator providing breathing gases to a patient, said controller allowing an operator to move about the ventilator and patient while controlling the ventilator, said controller comprising:

a control member actuatable by an operator to provide a signal for carrying out a control action in the ventilator;

communication means placing the control member in communication with the ventilator in a manner that allows the operator to move with respect to the ventilator and patient and to be at a distance from the ventilator, said communication means communicating said signal to the ventilator to control the ventilator; and means in said ventilator and in communication with said communication means for adjusting the sensitivity between the signal provided by said control member and the resulting control action in the ventilator.

4. A remote controller of claim 3 wherein said control member provides a signal having a magnitude range and wherein said adjusting means alters the sensitivity over the magnitude range of the signal.

5. A remote controller for a respiratory ventilator providing breathing gases to a patient, said controller allowing an operator to move about the ventilator and patient while controlling the ventilator, said controller comprising:

a control member actuatable by an operator to provide a signal for carrying out a control action in the ventilator;

communication means placing the control member in communication with the ventilator in a manner that allows the operator to move with respect to the ventilator and patient and to be at a distance from the ventilator, said communication means communicating said signal to the ventilator to control the ventilator; and means for establishing desired properties of linearity-non linearity between the signal provided by said control member and the resulting control action in the ventilator.

6. A remote controller of claim 5 wherein said control member provides a signal having a magnitude range and wherein said linearity-non linearity establishing means alters the linearity-non linearity properties over the magnitude range of the signals.

7. A remote controller for a respiratory ventilator providing breathing gases to a patient, said controller allowing an operator to move about the ventilator and patient while controlling the ventilator, said controller comprising:

a control member actuatable by an operator to provide a signal for carrying out a control action in the ventilator;

communication means placing the control member in communication with the ventilator in a manner that allows the operator to move with respect to the ventilator and patient and to be at a distance from the ventilator, said communication means communicating said signal to the ventilator to control the ventilator; and means in said ventilator and in communication with said communications means for establishing desired properties of linearity-non linearity between the signal provided by said control member and the resulting control action in the ventilator.

8. A remote controller of claim 7 wherein said control member provides a signal having a magnitude range and wherein said linearity-non linearity establishing means alters the linearity-non linearity properties over the magnitude range of the signal.

9. A remote controller for a respiratory ventilator providing breathing gases to a patient, said controller allowing an operator to move about the ventilator and patient while controlling the ventilator, said controller comprising:

a control member actuatable by an operator to provide a signal for carrying out a control action in the ventilator; and communication means placing the control member in communication with the ventilator in a manner that allows the operator to move with respect to the ventilator and patient and to be at a distance from the ventilator, said communication means communicating said signal to the ventilator to control the ventilator;

wherein said control member includes a displaceable, signal generating element for providing the signal; and wherein said element comprises variable resistance means.

10. A system suitable for use with medical apparatus, the system employing a signal indicative of a parameter relating to the apparatus or to a patient associated with the apparatus, the system providing a tactile feedback of the parameter to a user remote from the apparatus, said system comprising:

feedback means suitable for being placed in contact with a selected body portion of the user for generating a tactile sensation that can be experienced by the user; and communication means placing the feedback means in communication with the medical apparatus in a manner that allows the user, when in contact with said feedback means, to be distant from the medical apparatus and to move about the apparatus and patient to a desired location, said communication means communicating the signal indicative of the parameter to said feedback means, said feedback means employing said parameter signal to generate a tactile sensation to the body of the user corresponding to the parameter.

11. A system of claim 10 wherein said feedback means includes actuator means for generating a force on the selected body portion of the user.

12. A system of claim 11 wherein said actuator means comprises an electrical actuator means.

13. A system of claim 11 wherein said actuator means comprises a fluid operated actuator means.

14. A system of claim 13 wherein said fluid actuated means comprises a bladder.

15. A system of claim 11 wherein said actuator means comprises a linear actuator means.

16. A system of claim 11 wherein said actuator means comprises rotary actuator means.

17. A system of claim 10 further including means for adjusting the sensitivity between the parameter signal from the apparatus and the resulting tactile sensation generation.

18. A system of claim 17 wherein the apparatus provides a parameter signal having a magnitude range and wherein said adjusting means alters the sensitivity over the magnitude range of the signal.

19. A system of claim 10 including means in said medical apparatus and in communication with said communication means for adjusting the sensitivity between the parameter signal from the apparatus and the resulting tactile sensation generation.

20. A system of claim 19 wherein the apparatus provides a parameter signal having a magnitude range and wherein said adjusting means alters the sensitivity over the magnitude range of the signal.

21. A system of claim 10 including means for establishing desired properties of linearity-non linearity between the parameter signal from the apparatus and the resulting tactile sensation generation.

22. A system of claim 21 wherein the parameter signal has a magnitude range and wherein said linearity-non linearity establishing means alters the linearity-non linearity properties over the magnitude range of the signal.

23. A system of claim 10 including means in said apparatus and in communication with said communication means for establishing desired properties of linearity-non linearity between the parameter signal from the apparatus and the resulting tactile sensation generation.

24. A system of claim 23 wherein the parameter signal has a magnitude range and wherein said linearity-non linearity establishing means alters the linearity-non linearity properties over the magnitude range of the signal.

25. A system of claim 10 wherein said feedback means is further defined as suitable for being placed in contact with the hand of the user.

26. A system of claim 25 wherein said feedback means includes a trigger for being placed in contact with the fingers of the user, said feedback means including an actuator for said trigger operable by said parameter signal.

27. A system of claim 26 further defined as a remote tactile feedback system for medical apparatus comprising a ventilator, the ventilator providing a signal relating to the ventilation of a patient and wherein said feedback means generates a tactile sensation to a user indicative of a respiration characteristic.

28. A system according to claim 27 wherein said feedback means generates a tactile sensation of the patient airway pressure.

29. A system of claim 27 wherein said feedback means generates a tactile indication of the tidal volume of breathing gases delivered to the patient.

30. A system of claim 25 wherein said feedback means has a base for positioning the feedback means on a surface.

31. A system of claim 10 wherein said apparatus provides a plurality of signals indicative of parameters and wherein said system includes switch means for selecting the parameter to be monitored.

32. A system of claim 10 wherein said communication means communicates a plurality of signals indicative of parameters to said feedback means and wherein said feedback means generates tactile sensations to the body of the user incorporating a plurality of parameter signals.

33. A system of claim 10 further including second feedback means suitable for being placed in contact with a selected body portion of a further user for generating a tactile sensation that can be experienced by the further user; said second feedback means being in communication with one of said feedback means or the medical apparatus to provide a tactile sensation to the further user corresponding to the tactile sensation generated by said feedback means.

34. A system of claim 10 further defined as a remote tactile feedback system for medical apparatus comprising a ventilator, the ventilator providing a signal relating to the ventilation of a patient, and wherein said feedback means generates a tactile sensation to the user indicative of a respiration characteristic.

35. A system of claim 34 wherein said feedback means generates a tactile sensation of the patient airway pressure.

36. A system of claim 34 wherein the feedback means generates a tactile sensation of the tidal volume of breathing gases delivered to the patient.

37. A system of claim 10 including display means for displaying information for a user.

38. A system of claim 10 wherein said system provides a tactile feedback of a parameter comprising at least one of patient airway pressure, patient breathing gas flow, patient tidal volume, patient pulse rate, patient blood pressure, and patient arterial blood oxygen saturation.

39. A remote control and tactile feedback system for medical apparatus, the system allowing an operator to move about the medical apparatus or patient while controlling the apparatus and receiving a tactile feedback of a parameter, the system employing a signal indicative of a parameter relating to the apparatus or to a patient associated with the apparatus, said system comprising:

control means actuatable by an operator to provide a control signal for carrying out a control action in the medical apparatus;

feedback means suitable for being placed in contact with a selected body portion of the user for generating a tactile sensation that can be experienced by the user; and communication means placing the control means and feedback means in communication with the medical apparatus in a manner that allows the operator to move about the apparatus and patient and to be at a distance from the apparatus, said communication means communicating the control signal to the medical apparatus to control the apparatus, said communication means communicating the signal indicative of the parameter to said feedback means, said feedback means employing said parameter signal to generate a tactile sensation to the body of the user corresponding to the parameter.

40. A system of claim 39 wherein said feedback means includes actuator means for generating a force on the selected body portion of the user.

41. A system of claim 40 wherein said actuator means comprises an electrical actuator means.

42. A system of claim 40 wherein said actuator means comprises a fluid operated actuator means.

43. A system of claim 40 wherein said actuator means comprises a linear actuator means.

44. A system of claim 40 wherein said actuator means comprises rotary actuator means.

45. A system of claim 39 wherein said control member is actuatable to establish the presence or absence of a signal for carrying out a control action in the ventilator.

46. A system of claim 39 wherein said control member is actuatable to provide a variable magnitude signal for carrying out a control action in the ventilator.

47. A system of claim 46 for controlling the flow of breathing gases to a patient wherein said controller is further defined as including means for controlling the magnitude of the breathing gas flow to the patient in accordance with the magnitude of the control member signal.

48. A system of claim 47 for controlling the flow of breathing gases to a patient wherein said controller is further defined as including means to carry out a control action of providing a breathing gas flow magnitude to the patient that is proportional to the rate of change of the variable magnitude control member signal.

49. A system of claim 39 wherein said control member includes a displaceable, signal generating element for providing the signal.

50. A system of claim 49 wherein said element is a switch.

51. A system of claim 49 wherein said element comprises variable resistance means.

52. A system of claim 39 wherein said control means and feedback means comprise a common element.

53. A system of claim 52 wherein said common element is further defined as suitable for being placed in contact with the hand of the user.

54. A system of claim 53 wherein said common element includes a trigger for being placed in contact with the fingers of the user, said feedback means including an actuator for said trigger operable by said parameter signal.

55. A system of claim 39 further including a display for providing information to the operator.

56. A system of claim 39 including means for adjusting the sensitivity between the control or parameter signal and the respective resulting control action in the ventilator or tactile sensation generation.

57. A system of claim 56 wherein at least one of said signals has a magnitude range and wherein said adjusting means alters the sensitivity over the magnitude range of the signal.

58. A system of claim 39 including means in said ventilator and in communication with said communication means for adjusting the sensitivity between the control or parameter signal and the respective resulting control action in the ventilator or tactile signal generation.

59. A system of claim 58 wherein at least one of said signals has a magnitude range and wherein said adjusting means alters the sensitivity over the magnitude range of the signal.

60. A system of claim 39 including means for establishing desired properties of linearity-non linearity between the control or parameter and the respective resulting control action in the ventilator or tactile sensation generation.

61. A system of claim 60 wherein at least one of said signals has a magnitude range and wherein said linearity-non linearity establishing means alters the linearity-non linearity properties over the magnitude range of the signals.

62. A system of claim 39 including means in said ventilator and in communication with said communications means for establishing desired properties of linearity-non linearity between the control or parameter signal and the respective resulting control action in the ventilator or tactile sensation generation.

63. A system of claim 62 wherein at least one of said a signals has a magnitude range and wherein said linearity-non linearity establishing means alters the linearity-non linearity properties over the magnitude range of the signal.

64. A system of claim 39 wherein one of said control member or feedback means employs an electric signal.

65. A system of claim 39 wherein one of said control member or feedback means employs a fluidic signal.

66. A system of claim 39 wherein one of said control member or feedback means employs an analog signal.

67. A system of claim 39 wherein one of said control member or feedback means employs a digital signal.

68. A system of claim 39 wherein said communication means comprises a cable.

69. A system of claim 68 wherein said communication means comprises electrical means and wherein said cable contains electrical conductors.

70. A system of claim 68 wherein said communication means comprises optical means and said cable contains optical fiber means.

71. A system of claim 39 wherein said communication means comprises a telemetry link.

72. A system of claim 71 wherein said telemetry link employs invisible light.

73. A system of claim 71 wherein said telemetry link employs infrared radiation.

74. A system of claim 71 wherein said telemetry link is a radio telemetry link.

75. A system of claim 39 for controlling the flow of breathing gases to a patient and wherein said control means is further defined as providing a breathing gas flow control signal.

76. A system of claim 39 for controlling breathing gas pressures and wherein said control means is further defined as providing a breathing gas pressure control signal.

77. A system of claim 39 wherein said system generates a tactile sensation of a parameter comprising one of patient airway pressure, patient breathing gas flow, patient tidal volume, patient pulse rate, patient blood pressure, and patient arterial blood oxygen saturation.

78. A system of claim 77 wherein said feedback means generates a tactile sensation of the patient airway pressure.

79. A system of claim 77 wherein the feedback means generates a tactile sensation of the tidal volume of breathing gases delivered to the patient.

80. A system of claim 39 wherein said communication means communicates a plurality of signals indicative of parameters to said feedback means and wherein said feedback means generates tactile sensations to the body of the user incorporating a plurality of parameter signals.

81. A remote control and tactile feedback system for a respiratory ventilator, the system allowing an operator to move about the ventilator or patient while controlling the ventilator and receiving a tactile feedback of a parameter, the system employing a signal indicative of a parameter relating to the ventilator or to a patient associated with the apparatus, said system comprising:

a member suitable for being placed in the hand of the operator and having a trigger connected to a signal generator to provide a control signal for carrying out a control action in the ventilator, said member having actuator means for operating said trigger to generate a tactile sensation that can be experienced by the user; and communication means placing the signal generator and actuator means in communication with the ventilator in a manner that allows the operator to move about the apparatus and patient and to be at a distance from the apparatus, said communication means communicating the control signal to the ventilator to control the apparatus, said communication means communicating the signal indicative of the parameter to said actuator means to generate a tactile sensation to the body of the user corresponding to the parameter.

* * * * *